(12) United States Patent
Ashihara et al.

(10) Patent No.: US 6,221,625 B1
(45) Date of Patent: Apr. 24, 2001

(54) ENZYME-LABELED IMMUNOASSAY AND DEVICE THEREFOR

(75) Inventors: Yoshihiro Ashihara; Mitsuo Isomura, both of Saitama; Atsuka Sato, Tokyo, all of (JP)

(73) Assignee: Fujirebio Inc., Tokyo (JP)

( * ) Notice: Subject to any disclaimer, the term of this patent is extended or adjusted under 35 U.S.C. 154(b) by 0 days.

(21) Appl. No.: 09/017,214

(22) Filed: Feb. 2, 1998

(30) Foreign Application Priority Data

Apr. 23, 1997 (JP) .................................................... 9-118646

(51) Int. Cl.$^7$ .................................................... G01N 33/53
(52) U.S. Cl. ......................... 435/7.9; 435/7.71; 435/7.91; 435/7.92; 435/287.1; 435/287.2; 435/970; 436/518; 436/536; 436/537; 436/538; 436/514; 436/810; 422/56; 422/57; 422/58
(58) Field of Search ..................................... 435/7.9, 7.71, 435/7.91, 7.92, 287.1, 287.2, 970; 436/536, 537, 538, 518, 514, 810; 422/56, 57, 58

(56) References Cited

U.S. PATENT DOCUMENTS

| | | | |
|---|---|---|---|
| 4,585,792 | * | 4/1986 | Kasahara et al. ..................... 436/523 |
| 4,835,099 | * | 5/1989 | Mize et al. ............................ 436/536 |
| 5,296,347 | * | 3/1994 | LaMotte, III ......................... 436/538 |

FOREIGN PATENT DOCUMENTS

| | | |
|---|---|---|
| 0 271 731 | 6/1988 | (EP) . |
| 0 354 548 | 2/1990 | (EP) . |
| 0 512 390 | 11/1992 | (EP) . |
| WO 88/08536 | 11/1988 | (WO) . |

\* cited by examiner

*Primary Examiner*—Christopher L. Chin
(74) *Attorney, Agent, or Firm*—Oblon, Spivak, McClelland, Maier & Neustadt, P.C.

(57) ABSTRACT

An enzyme-labeled immunoassay is performed by the steps of allowing a test sample to react with an enzyme-labeled reagent, allowing a substrate to react with the enzyme to form a signal, and immobilising the enzyme-labeled reagent, with the prevention of a further signal formation from a predetermined time on after the immobilisation of the enzyme-labeled reagent, using an enzyme inhibitor. A device for performing this enzyme-labeled immunoassay includes an absorbent material capable of transporting a developing solution by capillary action, the absorbent material including (a) a developing liquid application zone, (b) an enzyme-labeled reagent zone containing an enzyme-labeled reagent, (c) a sample receiving zone, and (d) an indicator reagent zone capable of immobilising the enzyme-labeled reagent after the reaction of the test sample with the enzyme-labeled reagent in an amount dependent on the assay result, with an enzyme inhibitor being applied to a portion in the absorbent material upstream of the enzyme-labeled reagent zone, which enzyme inhibitor prevents the formation of a signal from a predetermined time on after the enzyme-labeled reagent is immobilised at the indicator reagent zone.

10 Claims, 2 Drawing Sheets

ENZYME-LABELED IMMUNOASSAY AND DEVICE THEREFOR

BACKGROUND OF THE INVENTION

1. Field of the Invention

The present invention relates to an enzyme-labeled immunoassay comprising the steps of allowing a test sample to react with an enzyme-labeled reagent, allowing a substrate to react with the enzyme to form a signal, and immobilising the enzyme-labeled reagent, with the prevention of a further signal formation from a pre- determined time on after the immobilisation of the enzyme-labeled reagent, using an enzyme inhibitor. The present invention also relates to a device for performing this enzyme-labeled immunoassay.

2. Discussion of Background

Recently immunoassays using an enzyme as a labeling material and a device comprising an absorbent material capable of transporting an enzyme-labeled reagent by capillary action, using a developing solution, are known as convenient and simple assays for the detection of analyte substances in biological fluids, and medicinal substances in test samples, utilizing immunoreactions (refer to, for example, Japanese Laid-Open Patent Application 61-145459, European Patent 186,799, Japanese Laid-Open Patent Application 63-501595, U.S. Patent 5,604,110 and European Patent 225,054). When using a test strip comprising such a device, for example, a test sample containing an analyte is allowed to react with an enzyme-labeled reagent, a substrate is then allowed to react with the enzyme to form a signal, and immobilising the enzyme-labeled reagent reacted with the test sample, using an immunoreactive substance in an indicator reagent zone, and in a predetermined period of time after the reaction of the test sample and the enzyme-labeled reagent, the degree of the formation of the signal, such as the coloring degree of the indicator reagent zone, is measured or evaluated, whereby the amount of the analyte contained in the test sample is assayed.

In order to prevent the formation of the signal (coloring or luminescence) except where enzyme-labeled reagent is immobilized at the indicator reagent zone, there is proposed an immunoassay test strip in which a signal formation inhibitor is contained therein to prevent the reaction between the enzyme and the substrate until the developing solution reaches the indicator reagent zone (Japanese Laid-Open Patent Application 1-503439, U.S. Patent 5,641,639, European Patent 312,565, Japanese Laid-Open Application 5-149951 and European Patent 512,390). In such an immunoassay using the above test strip, it is possible to prevent the formation of the signal up to the indicator reagent zone by providing a signal formation inhibitor zone upstream of the indicator reagent zone in terms of the transport direction of the developing solution, optionally with the provision of a signal initiation zone, whereby immunoassay can be carried out with high sensitivity for many analysis items.

However, in the immunoassay using the above-mentioned signal formation inhibitor, it is possible to inhibit the formation of the signal by the reaction between the enzyme and the substrate from the initiation of the assay with the application of the developing solution to the strip until the developing solution reaches the indicator reagent zone, but cannot inhibit the formation of the signal which continuously take place in the indicator reagent zone after a specific period of time.

Further, in the immunoassay using a coloring substrate, the degree of the coloring of the indicator reagent zone is evaluated by visual inspection or using a color difference meter after the reaction between the enzyme and the substrate for a predetermined period of time, whereby an assay result is obtained. In such a conventional immunoassay, when a negative or positive evaluation or judgement is performed, using the difference in the density of the coloring in the indicator reagent zone, the density of the coloring increases with time in the course of the assay, so that the evaluation or judgement may be changed from "negative" to "positive." Therefore, it is necessary to perform the assay with the assay time thereof being strictly controlled when the assay is performed, evaluating the changes in the density of the coloring in the indicator reagent zone.

Under such circumstances, there is demanded for an enzyme-labeled immunoassay which is capable of providing an accurate assay result, with the formation of a signal in the indicator reagent zone which depends upon the assay result, but without further signal formation from a predetermined time on in the course of the assay.

SUMMARY OF THE INVENTION

It is therefore a first object of the present invention to provide an enzyme-labeled immunoassay capable of providing an accurate assay result with the formation of a signal which depends upon the assay result, without further signal formation from a predetermined time on in the course of the assay.

A second object of the present invention is to provide a device for performing the above enzyme-labeled immunoassay.

The first object of the present invention can be achieved by an enzyme-labeled immunoassay comprising the steps of allowing a test sample to react with an enzyme-labeled reagent, allowing a substrate to react with the enzyme to form a signal, and immobilising the enzyme-labeled reagent, with the prevention of a further signal formation from a predetermined time on after the immobilisation of the enzyme-labeled reagent, using an enzyme inhibitor.

The second object of the present invention can be achieved by a device comprising an absorbent material capable of transporting a developing solution by capillary action, the absorbent material comprising (a) a developing solution application zone to which the developing solution is applied, (b) an enzyme-labeled reagent zone comprising an enzyme-labeled reagent, (c) a sample receiving zone to which a test sample is applied, and (d) an indicator reagent zone comprising an indicator reagent capable of immobilising the enzyme-labeled reagent after the reaction of the test sample with the enzyme-labeled reagent in an amount dependent on the assay result, which zones are sequentially arranged in the direction of the transport of the developing solution, with a substrate for an enzyme being applied to a portion in the absorbent material upstream of the enzyme-labeled reagent zone, and an enzyme inhibitor being applied to a portion in the absorbent material upstream of the enzyme-labeled reagent zone, which enzyme inhibitor prevents the formation of a signal which takes place by the reaction of the enzyme and the substrate, from a predetermined time on after the enzyme-labeled reagent is immobilised at the indicator reagent zone.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
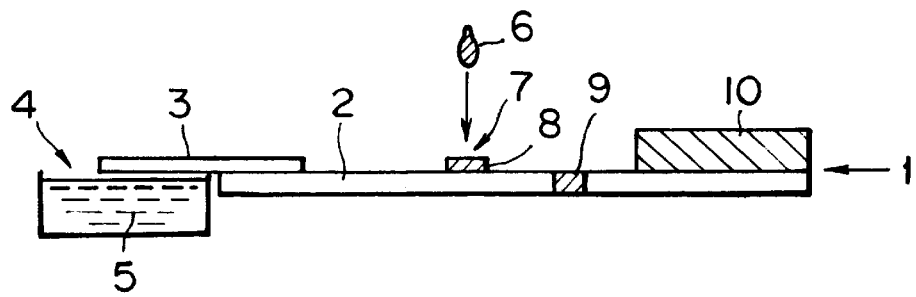
FIG. 1 is a cross-sectional diagram of a preferable example of a test strip for use in the enzyme-labeled immunoassay of the present invention.

With reference to FIG. 1, a preferable example of a device for performing the enzyme-labeled immunoassay of the present invention will now be explained.

As shown in FIG. 1, the example of the device comprises a test strip 1 comprising an absorbent material strip 2 capable of transporting a developing solution 5 by capillary action. Examples of a material for the absorbent material strip 2 are cellulose or nitro-cellulose derivatives such as cellulose and nitro-cellulose, filter paper made of glass fibers, and a porous film. There is no particular limitation to the size of the absorbent material strip 2, but it is preferable that the absorbent material strip 2 be in the form of a strip with a width of about 3 to 10 mm, a length of about 30 to 100 mm and a thickness of about 3 $\mu$m to 1 mm for handy use thereof.

At the opposite end portions of the absorbent material strip 2, there are provided a developing solution supply zone 3 comprising a developing solution supply pad, and a developing solution absorbing zone 10 comprising an water absorbing pad. These pads may be made of the same material as that for the absorbent material strip 2 or a water-absorbing material such as sponge and water-absorbing unwoven cloth. The developing solution supply zone 3 and the developing solution absorbing zone 10 are usually formed thicker than the absorbent material strip 2, but it is not an essential requirement for the developing solution supply zone 3 and the developing solution absorbing zone 10. The developing solution supply zone 3 and the developing solution absorbing zone 10 may also be formed by forming the opposite end portions of the absorbent material strip 2 into the developing solution supply pad and the developing solution absorbing pad.

The enzyme inhibitor for use in the present invention can be applied to a portion in the test strip 1 upstream of an enzyme-labeled reagent zone 8 in terms of the transport direction by capillary action of the developing solution 5. The enzyme inhibitor can be contained in either the developing solution 5 or the developing solution supply zone 3 or both the developing solution 5 and the developing solution supply zone 3. As the enzyme inhibitor for use in the present invention, any enzyme inhibitor can be used as long as the inhibitor can inhibits the reaction between the enzyme of the enzyme-labeled reagent and the substrate. An enzyme inhibitor suitable for the enzyme-labeled reagent can of course be selectively used.

Examples of the enzyme for use in the present invention are phosphatase such as alkaline phosphatase; peroxydase; and β-galactosidase.

When alkaline phosphatase is used as the enzyme, there can be used as the enzyme inhibitor, phosphoric acid; phosphates such as sodium phosphate and potassium phosphate; and phosphoric acid compounds such as phosphoric monoester, naphtholphosphoric acid, glycerophosphoric acid, phenyl phosphate, phosphoethanol amine, phosphorylcholine, and glucose phosphoric acid; and chelate compounds such as ethylenediaminetetraacetic acid, phenanthroline, and ethyleneglycosetetraacetic acid.

When peroxidase is used as the enzyme, reducing agents such as ascorbic acid, and azide compounds such as sodium azide and potassium azide can be used as the enzyme inhibitors.

Furthermore, when β-galactosidase is used as the enzyme, and galactose can be used as the enzyme inhibitor.

Even when any enzyme is used, an acid or a base can be used as the enzyme inhibitor in order to shift the pH of an indicator reagent zone 9 from the most appropriate pH for the enzyme.

When the enzyme inhibitor is applied to the developing solution supply zone 3, the enzyme inhibitor is applied to part of the developing solution supply zone 3 or to its entirety and then dried to form an enzyme inhibitor zone.

When the enzyme inhibitor is applied to the developing solution supply zone 3, the inhibition effect of the enzyme inhibitor in the indicator reagent zone 9 does not last and is vanescent, while when the enzyme inhibitor is contained in the developing solution 5, the inhibition effect of the enzyme inhibitor lasts long. Furthermore, when the enzyme inhibitor is applied to the developing solution supply zone 3 and is also contained in the developing solution 5, the enzyme inhibitor can completely prevent further signal formation from a predetermined time on after the immobilisation of the enzyme-labeled reagent. The position of the application of the enzyme inhibitor can be selected as desired in accordance with the application of the test strip 1.

The test strip 1 is further provided with a sample receiving zone 7 to which a test sample 6 is applied. In the sample receiving zone 7, the absorbent material is blocked in order to prevent the non-specific adsorption of proteins, and an enzyme-labeled reagent is contained therein in a dried state, which enzyme-labeled reagent comprises an immunoreactive substance such as an antibody or an antigen which is to be allowed to react with an analyte such as an antigen or an antibody is labeled with an enzyme.

It is preferable that the sample receiving zone 7 also be made as an enzyme-labeled reagent zone 8 composed of an enzyme-labeled reagent pad, whereby a large quantity of the enzyme-labeled reagent can be contained therein and a large quantity of a test sample can be applied thereto and therefore the assay sensitivity can be significantly improved.

There is no particular limitation to the material for the enzyme-labeled reagent pad as long as the material is water-absorbing. Examples of the material for the enzyme-labeled reagent are a sponge, water-absorbing unwoven cloth, and filter paper, made of a porous synthesized or natural polymer compound such as polyvinyl alcohol (PVA), cellulose or nitrocellulose, or made of a composite material composed of such polymer compounds. There is no particular limitation to the size of the enzyme-labeled reagent pad, but it is preferable that the enzyme-labeled reagent pad be of a size with a width of about 3 to 10 mm, a length of about 3 to 10 mm and a thickness of about 0.5 mm to 4 mm. The amount of the enzyme-labeled reagent that can be contained in the enzyme-labeled reagent pad differs depending upon the analyte to be tested, but is usually in the range of about 0.01 μg to 5 μg on a dried basis, which is greater in amount than the case where the enzyme-labeled reagent is directly applied to the absorbent material strip 2 and dried.

The sample receiving zone 7 can be provided in the absorbent material strip 2, not only in the enzyme-labeled reagent zone 8 as mentioned above, but also upstream of the water-absorbing zone 10 and upstream of the enzyme-labeled reagent zone 8, or downstream of the enzyme-labeled reagent zone 8 and up stream of the indicator reagent zone 9, in terms of the transport direction of the developing solution 5.

The indicator reagent zone 9 is positioned upstream of the water-absorbing zone 10 and downstream of the sample receiving zone 7 in terms of the transport direction of the developing solution 5. The indicator reagent zone 9 can be provided by fixing an immono-reactive substance, such as an antibody or an antigen which is allowed to react with an analyte such as an antigen or an antibody in the test sample 6, to the absorbent material strip 2 by chemical bonding or physical adsorption. An antibody or an antigen which is allowed to react with an analyte such as an antigen, or an antibody, may be bonded to an insoluble carrier, for instance, by chemical bonding such as covalent bonds, or physical adsorption, and contained in the absorbent material strip 2 before use. Examples of such insoluble carriers are particles prepared by insolubilizing a mixed liquid of gelatin, gum arabi and sodium hexameta-phosphate (Japanese Patent Publication 63-29223, U.S. Patent 4,416,813 and European Patent 62,968), polystyrene latex, erythrocytes of various animals, and glass fiber.

As the substrate for use in the present invention, various substrates can be selectively employed depending upon the enzyme to be used in combination therewith, the coloring, or the luminescence thereof.

Examples of substrates for use with alkaline phosphatase are disodium 5-bromo-4-chloro-3-indolyl-phosphorate (BCIP), disodium 5-bromo-6-chloro-3-indolyl-phosphorate, and examples of substrates for use with peroxidase are 1,2-phenylenediamine, 3,3',5,5'-tetramethylbenzidine, 2,2'-azinobis-3-ethylbenzothiazoline-6-sulfonic acid (ABTS).

Examples of substrates for use with β-galactosidase are 5-bromo-4-chloro-3-indolyl-β-galactopyranoside, and 5-bromo-6-chloro-3-indolyl-β-galactopyranoside.

Such a substrate can be applied to the test strip 1, upstream of the enzyme-labeled reagent zone 8 in terms of the transport direction of the developing solution 5 in the same manner as the above-mentioned enzyme inhibitor, and can be contained in one of the developing solution 5, the absorbent material strip 2, or the developing solution supply pad in the developing solution supply zone 3. It is preferable to provide a substrate zone in the absorbent material strip 2 or the developing solution supply zone 3, to which the substrate is applied and in which the applied substrate is dried, in order to perform the assay with high sensitivity.

In the enzyme-labeled immunoassay using the test strip 1 of the present invention, the test sample 6 is applied to the sample receiving zone 7 and at the same time, the developing solution 5 is applied to the developer solution supply zone 3. The developing solution 5 is held in a developing solution reservoir 4 which is disposed above or below the developing solution supply zone 3. For simple and handy assay, the developing solution reservoir 4 and the developing solution 5 are separated by a rupturable thin film, and by rupturing the thin film with the finger, the developing liquid 5 can be easily brought into contact with the developing solution supply zone 3. For making this assay easier and more handy, the test strip 1 and the developing solution reservoir 4 can be incorporated into a plastic case or the like in the form of a kit.

As the developing solution 5 for use in the present invention, varieties of buffer solutions such as acetic acid buffer, boric acid buffer, Tris-HCl buffer, and diethanolamine buffer, can be employed.

The test sample 6 applied to the sample receiving zone 7 reacts with the enzyme-labeled reagent in the enzyme-labeled reagent zone 8 and is carried by the developing solution 5 which flows from the developing solution supply zone 3 toward the indicator reagent zone 9 which is located downstream in terms of the transport direction of the developing solution 5. The test sample 6 which has reacted with the enzyme-labeled reagent in the enzyme-labeled reagent zone 8 reaches the indicator reagent zone 9. When the antigen or the antibody contained in the test sample 6 is trapped by an antigen or an antibody fixed to the indicator reagent zone 9 and immobilised there, since the antigen or the antibody contained in the test sample 6 is bonded to the enzyme-labeled reagent, the enzyme-labeled reagent is immobilized in the indicator reagent zone 9. The enzyme trapped in the indicator reagent zone 9 reacts with the substrate contained in the developing solution 5, so that a signal such as coloring or luminescence is formed in the indicator reagent zone 9. However, the enzyme inhibitor contained in the developing solution 5 subsequently hinders the reaction between the enzyme and the substrate, so that the formation of the signal is terminated in a predetermined period of time. Thus, when the antigen or the antibody to be assayed as an analyte is contained in the test sample, the formation of the signal can be observed in the indicator reagent zone 9. The developing solution 5 and other components which are not trapped by the indicator reagent zone 9 are then absorbed by the water-absorbing pad in the water-absorbing zone 10. When no analyte such as the antigen or the antibody is contained in the test sample, the enzyme-labeled reagent is not trapped by the indicator reagent zone 9, so that the enzyme-labeled reagent is absorbed by the water-absorbing pad in the water-absorbing zone 10 as it is and no signals are observed in the indicator reagent zone 9. By the formation of the signal or no formation of the signal, the presence or absence of the analyte such as the antigen or the antibody can be detected. The above-mentioned enzyme-labeled reagent and part of the substrate may react with the formation of the signal before the enzyme-labeled reagent reaches the indicator reagent zone 9. However, the developing solution 9 in the indicator reagent zone 9 contains a sufficient amount of the substrate for performing the enzyme-labeled immunoassay of the present invention.

In the above explanation, the enzyme-labeled reagent and the immunoreactive substance immobilized in the indicator reagent zone 9 are as being the antigen or the antibody. However, the term "the antigen or the antibody" in this specification means such substances that are capable of performing an antigen-antibody reaction (immunoreaction) and forming an immune complex, such as polychlonal antibodies and monochlonal antibodies, and fragments of these antibodies such as Fab, Fab and F(ab')$_2$, and hapten.

As mentioned above, analytes for the present invention are medicinal substances, such as theophylline, phenytoin, and valproic acid; and substances in organism, for example, low-molecular weight hormones, such as thyroxine, estrogen, and estradiol, cancer markers such as CEA, AFP, fecal hemoglobin (for FOBT: Fecal Occult Blood Test); viruses such as human immunodeficiency virus (HIV), adult T cell leukemia virus (HTLV-1), hepatitis B virus (HBV) and hepatitis C virus (HCV); high-molecular-weight hormones, such as thyroid stimulating hormone (TSH) and insulin, cytokine such as IL-1, IL-2 and IL-6; varieties of growth factors such as EGF and PDG; DNA and RNA of the above-mentioned viruses; antigens of proteins relating to inflammation such as CRP, and antibodies corresponding to the antigens. Examples of test samples for the assay of such antigens and antibodies are whole blood, serum, plasma, urine, body fluids such as lymph, and fecal extract.

Other features of this invention will become apparent in the course of the following description of exemplary embodiments, which are given for illustration of the invention and are not intended to be limiting thereof.

REFERENCE EXAMPLE 1
[Preparation of Rabbit Anti-hemoglobin polychlonal antibody (Fab)]

To 2 ml of rabbit anti-hemoglobin polychlonal antibody (200 mM sodium acetate buffer (pH 4.2)) with a concentration of 1 mg/ml, 40 µg of pepsin (Boeheringer Mannheim code: 108057) was added, and the mixture was incubated at 37° C. for 10 hours.

600 µg of a fraction of F(ab)$_2$ with a molecular weight of 100,000 was obtained, using Superdex 200 (16/60 gel filtration column)) (made by Pharmacia Co., Ltd.), which was equilibrated with a buffer solution (0.1 M sodium phosphate, 1 mM EDTA·2Na buffer solution (pH 7.0)) so as to adjust the pH to 7.0.

To 600 µg of the above fraction of F(ab)$_2$, 2-mercaptoethanolamine was added so as to adjust the concentration of the fraction of F(ab)$_2$ to 10 MM, and the mixture was incubated at 37° C. for 2 hours. An unreacted 2-mercaptoethanolamine was removed from the mixture, whereby a fraction of Fab was obtained in an amount of 500 µg.

REFERENCE EXAMPLE 2
[Preparation of maleimidized alkaline phosphatase]

To 2.0 mg of bovine intestinum tenue alkaline phosphatase (made by Oriental Yeast Co., Ltd.) (0.1 M sodium phosphate buffer (pH 7.0)) was added 16 µl of N-succinimidyl-4-maleimide butyric acid (GMBS made by Dojindo Laboratories Co., Ltd.) dissolved in DMF with a concentration of 10 mg/ml, and the mixture was incubated at 25° C. for 1 hour. An unreacted GMBS was removed from the mixture, whereby a maleimidized alkaline phosphatase was obtained in an amount of 1480 µg.

REFERENCE EXAMPLE 3
[Preparation of alkaline phosphatase-labeled rabbit anti-hemoglobin polychonal antibody]

To 500 µg of the rabbit anti-hemoglobin polychlonal antibody Fab fraction prepared in Reference Example 1, 1400 µg of the maleimidized alkaline phosphatase prepared in Reference Example 2, and the mixture was incubated at 25° C. for 2 hours. From this mixture, an alkaline phosphatase-labeled rabbit anti-hemoglobin polychonal antibody fraction with an average molecular weight of 190,000 was obtained in an amount of 400 µg, using Superdex 200 (16/60 gel filtration column))(made by Pharmacia Co., Ltd.).

EXAMPLE 1
[Immunoassay Test Strip for FOBT (Fecal Occult Blood Test)]

Figure 2:
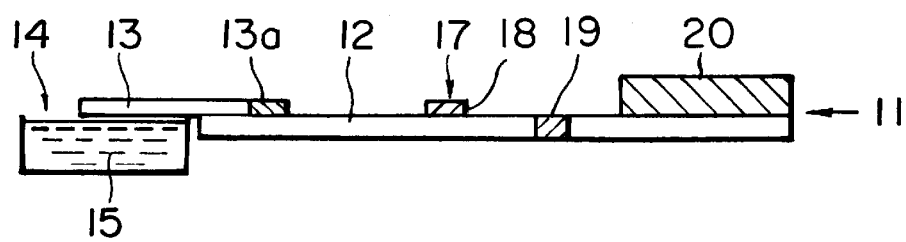
FIG. 2 is a cross-sectional diagram of an example of a test strip used in Examples 1 and 2 of the present invention.

As illustrated in FIG. 2, on an absorbent material strip 12 made of a 5 mm wide, 50 mm long cellulose film (made by Millipore Corp.), at a position of 15 mm from the right end thereof, an indicator reagent zone 19 is formed in the shape of a line so as to cross the absorbent material 12 by applying thereto a rabbit anti-hemoglobin polychlonal antibody in an amount of 1.33 µg and drying the applied rabbit anti-hemoglobin polychlonal antibody.

300 ng of a solution of the alkaline phosphatase-labeled rabbit anti-hemoglobin polychonal antibody prepared in Reference Example 3 was applied to a 5 mm wide, 5 mm long polyvinyl alcohol (PVA) sheet and dried, whereby a pad was prepared. This pad was provided on the absorbent material strip 12 at a position of about 25 mm from the right end thereof, which served not only as an enzyme-labeled zone 18 but also as a sample receiving zone 17 as illustrated in FIG. 2. A 10 mm wide, 20 mm long absorption pad 20 made of a filter paper (made by Millipore Corp.) was provided on the absorbent material strip 12 at a position of about 10 mm from the right end thereof.

As a developing solution 15, a 0.1 M CHES(N-cyclohexyl-2-aminoethane sulfonic acid)/NaOH (pH 10.0) buffer solution was employed. The developing solution 15 was placed in a developing solution reservoir 14 and the developing solution reservoir 14 was tightly sealed, using an aluminum sealing film, until the assay was initiated.

A 5 mm wide, 20 mm long filter paper (made by Millipore Corp.) was attached to the absorbent material strip 12 at a position of about 10 mm from the left end thereof, which constituted a developing solution supply zone 13 as illustrated in FIG. 2.

At the right end portion of the developing solution supply zone 13, a substrate zone 13a was formed by applying 100 µg of disodium 5-bromo-4-chloro-3-indolyl phosphate (BCIP) thereto and drying the applied BCIP as illustrated in FIG. 2, whereby an immunoassay test strip 11 was prepared.

To the developing solution 15, 4 mM monosodium phthalate was added, and 50 mM monosodium phthalate was applied to the developing solution supply zone 13, whereby an immunoassay test strip 11-1 of the present invention was prepared. The thus prepared immunoassay test strip 11-1 of the present invention is represented as "Test Strip 11-1 (Developing Solution+Filter Paper +)" in FIGS. 3 and 4.

The above prepared immunoassay test strip 11 was used as it was as a comparative immunoassay test strip 11-2, that is, without adding the above-mentioned 4 mM monosodium phthalate to the developing solution 15, and without applying the above-mentioned 50 mM monosodium phthalate to the developing solution supply zone 13. The thus prepared comparative immunoassay test strip 11-2 is represented as "Comparative Test Strip 11-2 (Developing Solution–Filter Paper–)" in FIGS. 3 and 4.

EXAMPLE 2

At room temperature, 25 µl of a fecal extract containing 20 ng/ml of hemoglobin, which was used as a positive standard sample, was applied to the sample receiving zone 17 of the immunoassay test strip 11-1 of the present invention, and the aluminum sealing film of the developing solution reservoir 14 was ruptured, whereby the developing solution 15 was brought into contact with the developing solution supply zone 13, and this assay was initiated.

The coloring of the indicator reagent zone 19 was visually inspected with time, and was also photographed, using a commercially available digital camera (Trademark "RD-175" made by Minolta Co., Ltd.) and subjected to image processing, using an image processing software EDAS (made by Cosmo Bio Co., Ltd.).

Figure 3:
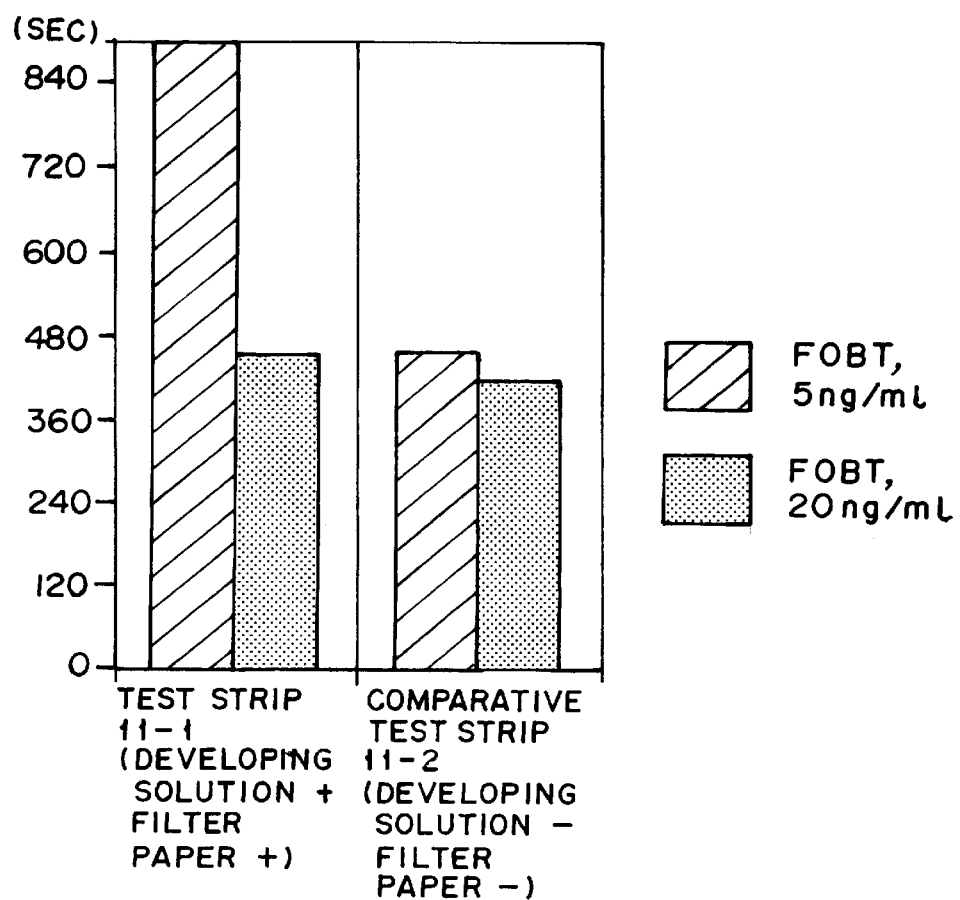
FIG. 3 is a graph showing the detection time of each of an FOBT positive standard analyte (hemoglobin 20 ng/ml) and an FOBT negative standard analyte (hemoglobin 5 ng/ml) when a test trip of the present invention and a comparative test strip.
Figure 4:
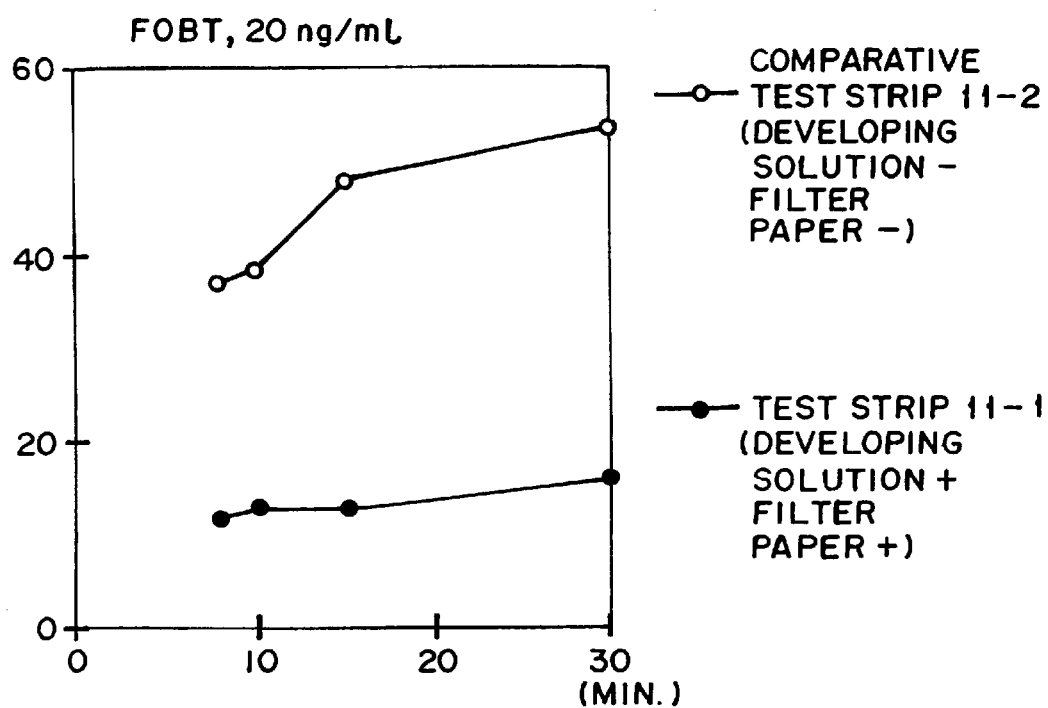
FIG. 4 is a graph showing the time dependency of the degree of the coloring of an indicator reagent zone of a test strip of the present invention and the time dependency of the degree of the coloring of an indicator reagent zone of a comparative test strip when an FOBT positive standard analyte (hemoglobin 20 ng/ml) was assayed.
Figure 5:
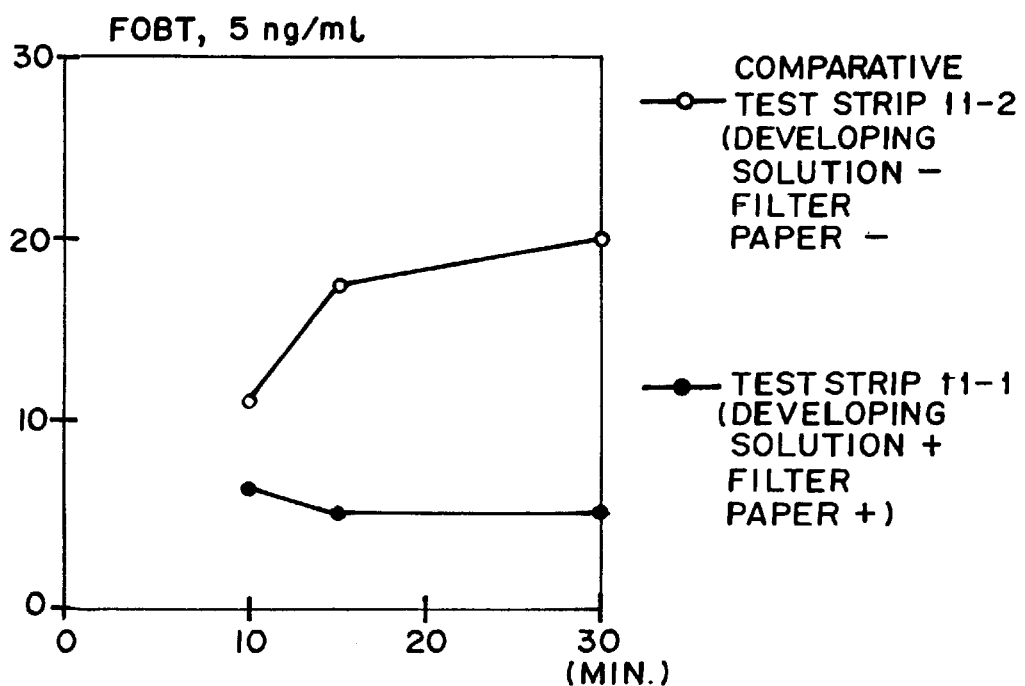
FIG. 5 is a graph showing the time dependency of the degree of the coloring of an indicator reagent zone of a test strip of the present invention and the time dependency of the degree of the coloring of an indicator reagent zone of a comparative test strip when an FOBT negative standard analyte (hemoglobin 5 ng/ml) was assayed.

The results are shown in TABLE 1 and FIGS. 3 to 5.

At room temperature, 25 μl of a fecal extract containing 5 ng/ml of hemoglobin, which was used as a negative standard sample, was applied to the sample receiving zone 17 of the immunoassay test strip 11-1 of the present invention, and the aluminum sealing film of the developing solution reservoir 14 was ruptured, whereby the developing solution 15 was brought into contact with the developing solution supply zone 13, and this assay was initiated.

The coloring of the indicator reagent zone 19 was visually inspected with time, and was also photographed, using the same commercially available digital camera as mentioned above and subjected to the same image processing as mentioned above.

The results are shown in TABLE 1 and FIGS. 3 to 5.

COMPARATIVE EXAMPLE

At room temperature, 25 μl of a fecal extract containing 20 ng/ml of hemoglobin, which was the same positive standard sample as used in Example 2, was applied to the sample receiving zone 17 of the comparative immunoassay test strip 11-2, and the aluminum sealing film of the developing solution reservoir 14 was ruptured, whereby the developing solution 15 was brought into contact with the developing solution supply zone 13 and this assay was initiated.

The coloring of the indicator reagent zone 19 was visually inspected with time, and was also photographed, using the same digital camera as used in Example 2 and subjected to the same image processing as in Example 2, using the same image processing software EDAS (made by Cosmo Bio Co., Ltd.).

The results are shown in TABLE 1 and FIGS. 3 to 5.

At room temperature, 25 μl of a fecal extract containing 5 ng/ml of hemoglobin, which was the same negative standard sample as used in Example 2, was applied to the sample receiving zone 17 of the comparative immunoassay test strip 11-2, and the aluminum sealing film of the developing solution reservoir 14 was ruptured, whereby the developing solution 15 was brought into contact with the developing solution supply zone 13, and this assay was initiated.

The coloring of the indicator reagent zone 19 was visually inspected with time and was also photographed, using the same commercially available digital camera as mentioned above, and subjected to the same image processing as mentioned above.

The results are shown in TABLE 1 and FIGS. 3 to 5.

TABLE 1

| | Evaluation of Results (Assay time: 8 minutes) | |
| --- | --- | --- |
| | Test Strip 11-1 (Developing Solution + Filter Paper +) | Comparative Test Strip 11-2 (Developing Solution − Filter Paper −) |
| Negative Standard (concentration of hemoglobin: 5 ng/ml) | − | + |
| Positive Standard (concentration of hemoglobin: 20 ng/ml) | + | + |

As can be seen from the above, when Test Strip 11-1 (Developing Solution+Filter Paper+) was used, a clear cut distinction was made between the negative standard and the positive standard in the course of the 8-minute assay time, while when Test Strip 11-2 (Developing Solution−Filter Paper−) was used, no distinction was made between the negative standard and the positive standard in the course of the 8-minute assay time.

FIG. 3 shows that when Test Strip 11-1 (Developing Solution+Filter Paper+) was used, the difference in the detection time between the positive standard and the negative standard was 440 seconds, and with respect to the negative standard, the evaluation result remained negative for 15 minutes after the imitation of the assay, while when Test Strip 11-2 (Developing Solution−Filter Paper−) was used, the difference in the detection time between the positive standard and the negative standard was only 41 seconds.

FIGS. 4 and 5 show that when Test Strip 11-1 (Developing Solution+Filter Paper+) was used, the coloring did not develop after a predetermined time on from the detection time, with respect to both the positive standard and the negative standard, while when Test Strip 11-2 (Developing Solution−Filter Paper−) was used, the coloring developed with time.

Thus, in the enzyme-labeled immunoassay using the test strip of the present invention, the change in the coloring of the indicator reagent zone is much smaller than that in the conventional enzyme-labeled immunoassay after a predetermined time on from the detection time, so that the evaluation or judgement can be performed even after the detection time. For example, in the case of FOBT (Fecal Occult Blood Test), the coloring of the indicator reagent zone can be substantially stopped after a predetermined negative or positive judgement (for instance 8 minutes) on, so that the judgement can be performed anytime after the period of 8 minutes. Thus, the enzyme-labeled immunoassay of the present invention is effective for performing simple and accurate positive or negative judgement or evaluation of an analyte in accordance with the difference in the color developed in the indicator reagent zone, without the necessity for the control of the detection time.

Japanese Patent Application No. 9-118646 filed Apr. 23, 1997 is hereby incorporated by reference.

What is claimed is:

1. An enzyme-labeled immunoassay comprising the steps of:

provid ing an absorbent material capable of transporting a developing solution by capillary action, applying a test sample containing an analyte to the absorbent material, allowing the analyte to react with an enzyme-labeled reagent, the reaction being allowed in the absorbent material, immobilizing the reacted enzyme-labeled reagent, allowing a substrate to react with the immobilized enzyme to form a signal, wherein, by the formation of the signal or no formation of the signal, a presence or absence of the analyte is detected, preventing a further signal formation from a predetermined time on after the immobilization of the enzyme-labeled reagent, using an enzyme inhibitor transported in the absorbent material, and evaluating the formation of the signal, whereby the presence of the analyte contained in the test sample is detected.

2. The enzyme-labeled immunoassay of claim 1, wherein the absorbent material comprises a enzyme-labeled reagent zone containing an enzyme-labeled reagent and an indicator reagent zone containing an indicator reagent.

3. The enzyme-labeled immunoassay of claim 2, wherein the analyte reacts with an enzyme-labeled reagent in the enzyme-labeled reagent zone wherein the analyte and the enzyme labeled reagent form an immune complex by the reaction.

4. The enzyme-labeled immunoassay of claim 3, wherein the immune complex is transported to the indicator reagent zone.

5. The enzyme-labeled immunoassay of claim 2, wherein the enzyme inhibitor is applied to the absorbent material so that the enzyme inhibitor reaches the indicator reagent zone later than the substrate.

6. The enzyme-labeled immunoassay as claimed in claim 1, wherein said enzyme is phosphatase, and said enzyme inhibitor is selected from the group consisting of a phosphoric acid compound and a chelate compound.

7. The enzyme-labeled immunoassay as claimed in claim 6, wherein said phosphoric acid compound is selected from the group consisting of phosphoric acid, phosphate, phosphoric monoester, naphtholphosphoric acid, glycerophosphoric acid, phenylphosphate, phosphoethanolamine, phosphorylcholin, and glycose phosphoric acid.

8. The enzyme-labeled immunoassay as claimed in claim 6, wherein said chelate compound is selected from the group consisting of ethylenediaminetetraacetic acid, phenanthroline, and ethyleneglycosetetraacetic acid.

9. The enzyme-labeled immunoassay as claimed in claim 1, wherein said enzyme is peroxidase, and said enzyme inhibitor is selected from the group consisting of a reducing compound and an azide compound.

10. The enzyme-labeled immunoassay as claimed in claim 1, wherein said enzyme is β-galactosidase, and said enzyme inhibitor is galactose.

* * * * *